United States Patent [19]

Goodman et al.

[11] Patent Number: 4,900,539
[45] Date of Patent: Feb. 13, 1990

[54] RADIOHALOGENATED THIENYLETHYLAMINE DERIVATIVES FOR EVALUATING LOCAL CEREBRAL BLOOD FLOW

[75] Inventors: Mark M. Goodman, Knoxville; Furn F. Knapp, Jr., Oak Ridge, both of Tenn.

[73] Assignee: The United States of America as represented by the United States Department of Energy, Washington, D.C.

[21] Appl. No.: 288,349

[22] Filed: Dec. 22, 1988

[51] Int. Cl.[4] .................... A61K 49/02; C07D 333/12
[52] U.S. Cl. ........................ 424/1.1; 549/74; 424/9
[58] Field of Search ............................ 424/1.1; 549/74

[56] References Cited
U.S. PATENT DOCUMENTS

| | | | |
|---|---|---|---|
| 2,367,702 | 1/1945 | Van Zoeren | 549/74 |
| 4,360,511 | 11/1982 | Baldwin et al. | |
| 4,458,086 | 7/1984 | Chekroun et al. | 549/74 |
| 4,482,718 | 11/1984 | Chekroun et al. | 549/74 X |

FOREIGN PATENT DOCUMENTS 0068979  1/1983  European Pat. Off. .............. 549/74

OTHER PUBLICATIONS

Fernandez-Tome, et al., "Relation Between Locomotor Hyperactivity Induced by P-Chloroamphetamine in Rats and Uptake of $^3$H-Dopamine," Arch, Farmacol Toxicol 1979, 5(3), 169–171.

David E. Kuhl et al., "Quantifying Local Cerebral Blood Flow by N-Isopropyl-p-[123]Iodamphetamine (IMP) Tomography," Oct. 15, 1981, pp. 196–203.

Hank F. Kung, et al., "A New Brain Perfusion Imaging Agent:[1-123]HIPDM:N,N,N'-Trimethyl-N'-[2-Hydroxy-3-Methyl-5-Iodobenzyl]-1,3-Propanediamine," Jun. 3, 1982, pp. 66–72.

Primary Examiner—John S. Maples
Attorney, Agent, or Firm—Katherine P. Lovingood; Stephen D. Hamel; William R. Moser

[57] ABSTRACT

Radiopharmaceuticals useful in brain imaging comprising radiohalogenated thienylethylamine derivatives. The compounds are 5-halo-thiophene-2-isopropyl amines able to cross the blood-brain barrier and be retained for a sufficient length of time to allow the evaluation or regional blood flow by radioimaging of the brain.

12 Claims, 1 Drawing Sheet

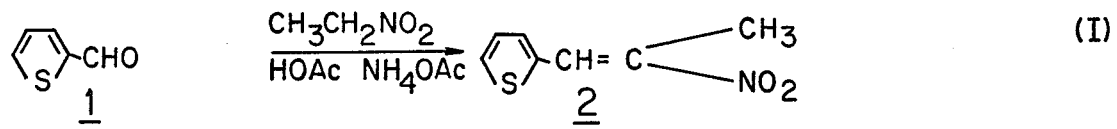 (I)
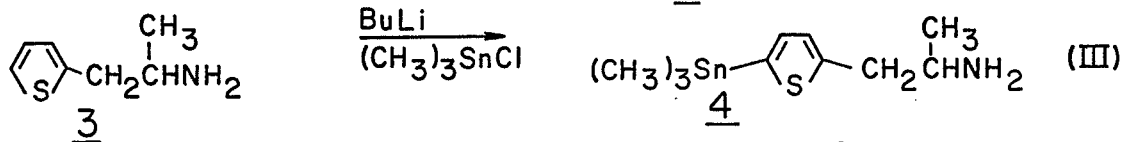 (II)
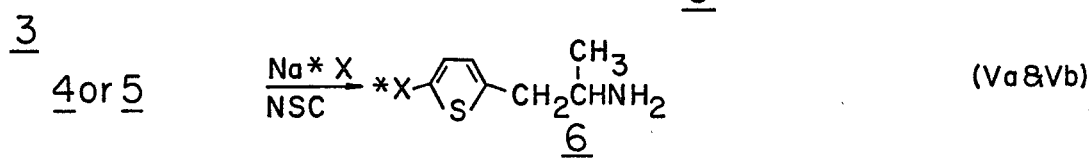 (III)
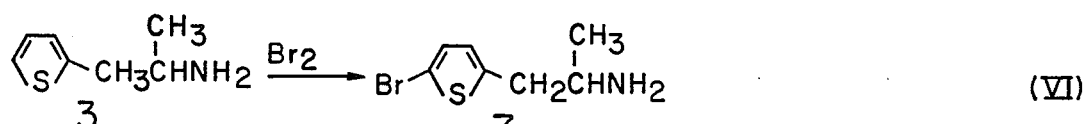 (IV)
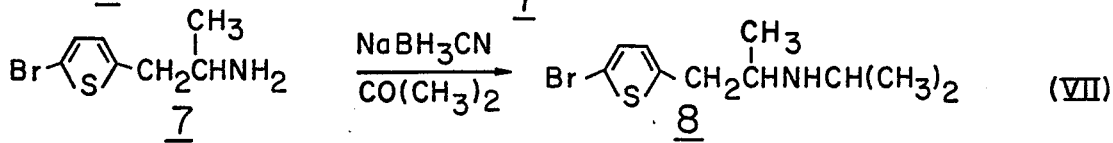 (Va & Vb)
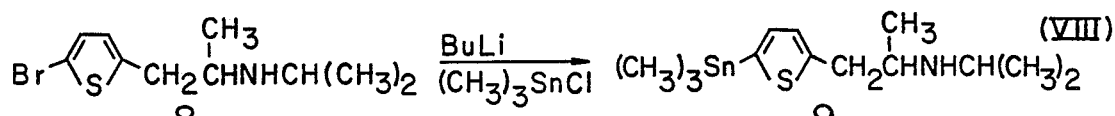 (VI)
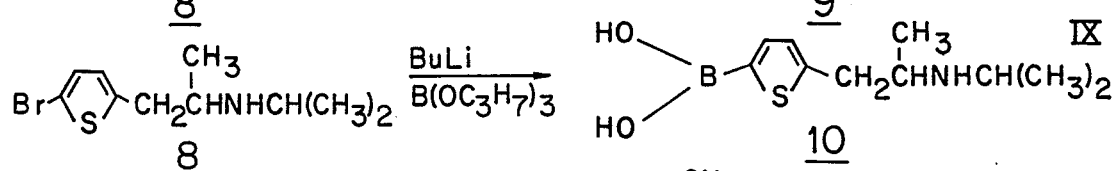 (VII)
(VIII)
IX
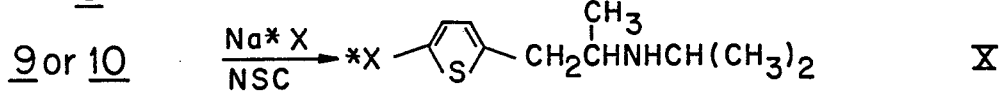 X

RADIOHALOGENATED THIENYLETHYLAMINE DERIVATIVES FOR EVALUATING LOCAL CEREBRAL BLOOD FLOW

This invention relates to radiopharmaceuticals useful in brain imaging, and more particularly to radiohalogenated thienylethylamine derivatives for evaluating cerebral blood flow and was developed pursuant to a contract with the United States Department of Energy.

BACKGROUND OF THE INVENTION

Stroke, brought on by cerebrovascular disease, is a leading cause of death and permanent disability in the United States. The life threatening nature of the disease is motivation for the development of new diagnostic techniques to determine the prognosis of patients with cerebrovascular disease during the early hours after onset of symptoms, when reversible brain injury can be aided by acute interventions.

Diagnostic techniques presently being used, such as computed tomography scans, do not routinely detect brain damage until a few days after the onset of stroke. A better method is nuclear medicine imaging using radiolabeled amines which rapidly cross the normal blood brain barrier. Perfusion defects can be detected early using this technique since the scans mapping regional blood flow immediately display damage in patients who suffer strokes.

Two radioiodinated brain imaging amines that have been developed are N-isopropyl-p-iodoamphetamine (IMP) and N,N,N'-trimethyl-N'-(2-hydroxyl-3-methyl-5-iodobenzyl)-1,3-propanediamine (HIPDM). IMP has shown an advantage over HIPDM of having almost twice the amount of activity in the brain five minutes after administration, leading to clearer images. It also clears the lungs faster resulting in better images since the scattering of high energy photons from the lung region is less. This minimizes the degradation of the brain image. These compounds are prepared by first synthesizing a halogenated precursor and then labeling by isotopic exchange. However, there are limitations to this synthetic approach. The specific activity is generally low due to presence of unlabeled starting material and the exchange reaction is slow and must be preformed at high temperatures. It is therefore necessary to provide compounds for efficient imaging of cerebral blood flow that are easy to make and result in clear images.

SUMMARY OF THE INVENTION

In view of the above mentioned need it is an object of this invention to provide compounds for imaging cerebral blood flow in warm blooded animals that have high specific activity in the brain as compared with other locations in the body.

It is another object of this invention to provide brain imaging compounds that can be made without resulting in dilution of the imaging effect by unlabeled starting material.

It is another object of this invention to provide brain imaging compounds that can be made by radiohalogenation at low temperatures.

It is a further object of this invention to provide brain imaging compounds that can be used in conjunction with nuclear scanning technology to render a distinct image of the brain. Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein, the composition of matter of this invention may comprise radiohalogenated thienylmonoamines having the structure

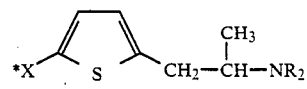

wherein *X is a radiohalogen and R is H or alkyl or aryl.

The invention is also a radiopharmaceutical kit comprising 2-(2-aminopropyl)-5-trimethylstannylthiophene, starting material for the unsubstituted imaging compound which can be radiohalogenated. The invention is also a kit comprising 2-(2-aminopropyl)-5-dihydroxyboranethiophene. Treatment of either of these compounds by iodestannylation with sodium radiohalide and N-chlorosuccinimide produces 2-(2-aminopropyl)-5-radiohalothiophene.

The invention is also a process for radioimaging wherein a compound as described above is mixed with a suitable administering medium. This mixture is injected into a warm blooded animal, allowed to cross the blood-brain barrier and a radioimage is recorded using standard radioimaging techniques.

The advantages of the invention include a simple synthesis route and a compound which is less diluted with nonradioactive halogen than the compounds of the prior art resulting in either a clearer image or a lower dose, depending on one's objective.

BRIEF DESCRIPTION OF THE DRAWING

The FIGURE represent a series of reactions for making the various compounds discussed and claimed in the application.

DETAILED DESCRIPTION OF THE PREFERRRED EMBODIMENT

Prior art brain imaging compounds IMP and HIPDM were routinely prepared by making a nonradioactive halogenated precursor and then substituting the nonradioactive halogen with a radiohalogen by isotopic exchange. The problems with this approach were that the specific activity was normally low due to the presence of unlabeled starting material and the isotopic exchange reaction was slow and had to be preformed at high temperature. A promising labeling technique is halodemetallation which quickly gives high radiochemical yields at low temperatures. Accordingly, the use of thiophene 2-substituted tissue specific agents are of interest because the reactive 5-position of the thiophene ring undergoes facile coupling to a variety of metals, as well as direct reaction with halogen.

The radiopharmaceuticals are prepared by first preparing intermediates which are then radiohalogenated to form the product. To prepare these intermediates, as structurally illustrated in the FIGURE, thiophene-2- carboxaldehyde (1), which can be acquired from a chemically supplier, is treated in the presence of acetic acid and sodium acetate with nitroethane to give 1-(2-thienyl)-2-nitropropene (2), Reaction I. Although acetic acid and ammonium acetate are present in the preferred embodiment, other combinations such as nitroethane and ammonium acetate, can also be used instead. This compound is then reduced with $B_2H_6$ to form 2-(2-aminopropyl)-thiophene (3), Reaction II. Lithiation of (3) with n-butyl lithium followed by treatment with trimethyl tin chloride gave an intermediate compound, 2-(2-aminopropyl)-5-trimethylstannylthiophene (4), Reaction III. Halogenation with sodium radiohalide and N-chlorosuccinimide produces 2-(2-aminopropyl)-5-radiohalothiophene (6), Reaction Va. Therefore, compound (4) can be sold as a kit comprising the starting material which is then radiohalogenated at the location where the radiopharmaceutical is to be administered.

Another intermediate can also be prepared that will also undergo radiohalogenation at the location of administration. Compound (3) is treated with n-butyl lithium and then $B(OC_3H_7)_3$ to form the [hydroxyboride](5), Reaction IV. This compound is the radiohalogenated using sodium radiohalide and N-chlorosuccinimide, Reaction Vb. Thus, the compound (5) can also comprise a kit that is used as starting material to form product (6).

In addition to the unsubstituted amines, substituted amines can also be made. Treatment of (3) with bromine gives 2-(2-aminopropyl)-5-bromothiophene (7), Reaction VI. To make substituted amines such as N-alkylated or N-arylated radiohalogenated thienylisopropylamine derivatives, unsubstituted compound (7) is subjected to reductive alkylation or arylation by sodium cyanohybridoborate and an alkyl or aryl substituted aldehyde or ketone. Reaction VII is representative of isopropyl substitution. This results in an N-substituted bromothiophene (8) which can be metallated in the 5 position using a variety of metallation reactions such as stannylation to render intermediate (9), Reaction VIII, and treatment with $B(OC_3H_7)_3$ to produce a hydroxyboride intermediate (10), Reaction IX. Again using sodium radiohalide and N-chlorosuccinimide, either of these intermediates can be converted to the N-substituted radiopharmaceutical (11), the thienyl analogue of IMP, one of the previously developed compounds. Key intermediates that can also comprise kits are compounds (9) and (10).

EXAMPLE

The Table shows the tissue distribution of two radiohalogens in Fisher rats. Bromine-82 labeled compound corresponding to 7 showed good brain uptake and retention in rats. The second model agent, iodine-125 compound corresponding to 6 showed high brain uptake and good retention with high brain-to-blood ratios.

TABLE
TISSUE DISTRIBUTION OF 5-HALOTHIOPHENE-
2-ISOPROPYLAMINES IN FISHER RATS
Mean Brain, % Dose/gm (Mean Brain:Blood)

| Halogen | 5 min | 30 min | 60 min |
|---------|-------|--------|--------|
| I—125   | 2.77 (6.0) | 2.51 (3.7) | 1.42 (2.1) |
| Br—82   | 2.70 (10.4) | 2.30 (4.1) | 1.67 (2.2) |

These preliminary studies indicate that I-123, I-122 and Br-75 5-substituted-thiophene-2-isopropyl amines would also demonstrate similar retention in the brain and allow the study alterations in local cerebral blood flow.

The compounds are used by mixing with a suitable administering medium, administering the mixture to a warm blooded animal by intravenous injection, allowing the mixture to cross the blood-brain barrier and recording a radioimage using radioimaging techniques. The amount of compound to be used can easily be determined by persons of ordinary skill in the art.

We claim:

1. A composition of matter comprising a radiohalogenated thienylmonoamine having the structure

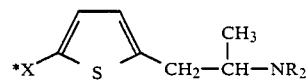

wherein *X is a radiohalogen and R is H or alkyl or aryl.

2. The composition of matter of claim 1 comprising

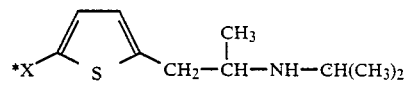

3. The composition of matter of claim 1 wherein said radiohalogen is selected from the group I-122, I-123, I-125, Br-75 and Br-82.

4. The composition of matter of claim 2 wherein said radiohalogen is selected from the group I-122, I-123, I-125, Br-75 and Br-82.

5. The composition of matter of claim 3 wherein said radiohalogen is selected from the group I-125 and Br-82 and said R is selected from the group H.

6. The composition of matter of claim 4 wherein said radiohalogen is selected from the group I-125 and Br-82.

7. A process for radioimaging comprising:
   mixing with a suitable administering medium a radiohalogenated thienylmonoamine having the structure

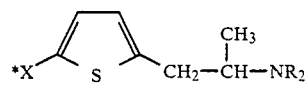

wherein *X is a radiohalogen and R is H or alkyl or aryl;
   injecting an effective amount of said mixture into a warm blooded animal;
   allowing said mixture to cross the blood-brain barrier; and recording a radioimage.

8. The process of claim 7 wherein said radiohalogenated thienylmonoamine comprises

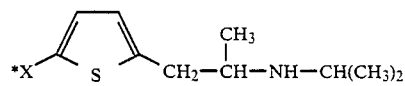

9. The process of claim 7 wherein said radiohalogen is selected from the group I-122, I-123, I-125, Br-75 and Br-82.

10. The process of claim 8 wherein said radiohalogen is selected from the group I-122, I-123, I-125, Br-75 and Br-82.

11. The process of claim 9 wherein said radiohalogen is selected from the group I-125 and Br-82 and said R is selected from the group H.

12. The process of claim 10 wherein said radiohalogen is selected from the group I-125 and Br-82.

* * * * *